United States Patent
Vogt et al.

(10) Patent No.: US 9,649,470 B2
(45) Date of Patent: May 16, 2017

(54) BREATH PACING APPARATUS, AND METHOD FOR PACING THE RESPIRATION OF A PERSON

(75) Inventors: Juergen Vogt, Eindhoven (NL); Jan Martijn Krans, Den Bosch (NL); Jia Du, Eindhoven (NL); Tim Johannes Willem Tijs, Helmond (NL); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 80 days.

(21) Appl. No.: 13/825,022

(22) PCT Filed: Sep. 14, 2011

(86) PCT No.: PCT/IB2011/054019
§ 371 (c)(1),
(2), (4) Date: Mar. 19, 2013

(87) PCT Pub. No.: WO2012/042419
PCT Pub. Date: Apr. 5, 2012

(65) Prior Publication Data
US 2013/0190554 A1    Jul. 25, 2013

(30) Foreign Application Priority Data
Sep. 28, 2010 (EP) .................................. 10180615

(51) Int. Cl.
*A61M 21/02* (2006.01)
*A61M 21/00* (2006.01)
*A63B 23/18* (2006.01)

(52) U.S. Cl.
CPC ............ *A61M 21/02* (2013.01); *A61M 21/00* (2013.01); *A63B 23/185* (2013.01);
(Continued)

(58) Field of Classification Search
CPC .......... A61M 21/00; A61M 2021/0022; A61M 2021/0088; A61M 21/02; A61M 2205/50; A61M 2205/10; A63B 23/185
(Continued)

(56) References Cited

U.S. PATENT DOCUMENTS

| | | | |
|---|---|---|---|
| 4,606,328 A | 8/1986 | Thoman | |
| 5,395,301 A | 3/1995 | Russek | |

(Continued)

FOREIGN PATENT DOCUMENTS

| | | | |
|---|---|---|---|
| CN | 101711121 A | 5/2010 | |
| CN | 102246120 A | 11/2011 | |

(Continued)

OTHER PUBLICATIONS

Parness, Amy, Guttman, Ed, Brumback, Christine. "Squeeze Me: A Portable Biofeedback Device for Children." Fifth International Conference on Ubiquitous Computing. NY, 2003.
(Continued)

*Primary Examiner* — Navin Natnithithadha
*Assistant Examiner* — Sunita Reddy

(57) ABSTRACT

A breath pacing apparatus and a method for pacing a respiration of a person include a haptic output unit with a variable haptically perceivable feature. The haptic output unit is configured to change the haptically perceivable feature periodically according to a sequence of desired respiration cycles, where a characteristic of the change of the haptically perceivable feature is related to a length of the respiration cycles in the sequence of desired respiration cycles.

19 Claims, 1 Drawing Sheet

(52) U.S. Cl.
CPC ............... *A61M 2021/0022* (2013.01); *A61M 2021/0088* (2013.01); *A61M 2205/10* (2013.01); *A61M 2205/50* (2013.01)

(58) Field of Classification Search
USPC ....... 600/26–28; 128/897–899; 606/202, 203
See application file for complete search history.

(56) References Cited

U.S. PATENT DOCUMENTS

| | | | |
|---|---|---|---|
| 6,062,216 A * | 5/2000 | Corn | 128/204.23 |
| 6,662,032 B1 * | 12/2003 | Gavish et al. | 600/323 |
| 6,981,943 B2 | 1/2006 | Noguchi | |
| 7,691,049 B2 * | 4/2010 | Wood et al. | 600/26 |
| 2005/0131273 A1 | 6/2005 | Asano et al. | |
| 2006/0047202 A1 * | 3/2006 | Elliott | 600/485 |
| 2007/0114206 A1 * | 5/2007 | Mitrovic et al. | 216/59 |
| 2007/0173730 A1 * | 7/2007 | Bikko | A61B 5/0803 600/538 |
| 2007/0179334 A1 | 8/2007 | Groves et al. | |
| 2007/0203433 A1 * | 8/2007 | Murphy | 601/15 |
| 2008/0234785 A1 | 9/2008 | Nakayama et al. | |
| 2009/0114216 A1 * | 5/2009 | Hung et al. | 128/200.24 |
| 2009/0192402 A1 * | 7/2009 | Corn | 600/534 |
| 2010/0112537 A1 | 5/2010 | Dobson | |
| 2010/0125226 A1 | 5/2010 | Hare | |
| 2010/0240945 A1 * | 9/2010 | Bikko | G10L 21/00 600/28 |

FOREIGN PATENT DOCUMENTS

| | | | | |
|---|---|---|---|---|
| DE | 20103442 U1 | 2/2001 | | |
| DE | 20103443 U1 | 2/2001 | | |
| DE | 20205187 U1 | 4/2002 | | |
| FR | 2834875 A1 | 1/2002 | | |
| GB | 2397761 A | 8/2004 | | |
| GB | 2421441 A | 6/2006 | | |
| JP | 02336358 A | 11/2002 | | |
| JP | 2002336357 A | 11/2002 | | |
| JP | 2006055625 A | 3/2006 | | |
| JP | 2008229248 A | 10/2008 | | |
| WO | 8602815 A1 | 5/1986 | | |
| WO | 2008139380 A2 | 5/2008 | | |
| WO | WO2009002577 A1 | 12/2008 | | |
| WO | WO 2009133517 A1 * | 11/2009 | ............ | A61B 5/024 |
| WO | WO2010068574 A1 | 6/2010 | | |
| WO | 2011045709 A1 | 4/2011 | | |

OTHER PUBLICATIONS

Hanlon, "The Stresseraser: Handheld Biofeedback Device to Offer Relief From Physical, Mental and Emotional Stress", Health & Wellbeing, Downloaded From http://www.gizmag.com/go/4472/, Aug. 22, 2005, p. 1-7.

Ferriss, "Sleep Better. Work Better. Live Better", Fall Asleep Naturally With Nightwave, Downloaded From http://www.nightwave.com/index.php, Feb. 22, 2016.

* cited by examiner

BREATH PACING APPARATUS, AND METHOD FOR PACING THE RESPIRATION OF A PERSON

FIELD OF THE INVENTION

The invention relates to a breath pacing apparatus and to a method for pacing the respiration of a person.

BACKGROUND OF THE INVENTION

Slow, regular breathing is considered to be beneficial for relaxation. To support the breathing process, breath pacing devices are known to provide a sequence of desired respiration cycles that corresponds to a regular breathing rhythm. These respiration cycles, each comprising an inhale phase and a subsequent exhale phase, are displayed to a user in form of an output signal that is easily perceivable by the user. For this purpose an optical signal can be used, i.e. a light that changes it intensity, color or shape according to the desired respiration cycles. For example, breath pacers are known that can be used in bed by a person to reduce sleep onset latency. This breath pacer projects a light spot of slowly varying size on the ceiling of the bedroom. However, light projections require at least a minimum of attention by the user and can be found disturbing by other persons. This also stands for audible cues to pace the user's respiration, because an audio signal is always hearable to another person present in the room or requires the user to wear headphones. However, the output signal representing the respiration cycles can also be haptically perceivable as a characteristic of a haptic output unit like, for example, a pad or a ball that increases or decreases its size or shape periodically.

To support the relaxation of a person using a breath pacing apparatus, it is beneficial to mimic a typical human breathing rhythm related to increasing relaxation as good as possible. For example, the length of the guiding respiration cycles may increase with time, i.e., each subsequent respiration cycle is longer than the preceding one, to increase the chance for relaxation. One problem arising with haptic output units is that with increasing length of the respiration cycles, it becomes more difficult to feel the change of the haptically perceivable feature and to follow the respiration rhythm. For example, a haptic output unit like an inflatable pad may increase its thickness from the beginning of one respiration cycle to the end of the inhale phase, reaching its maximum thickness, and beginning to decrease its thickness at the transition from the inhale phase to the exhale phase, reaching its minimum thickness again at the end of the cycle. The longer the cycle becomes, the more difficult it is for the user to feel the "turning point" at which the pad reaches its maximum thickness and further the transition from the exhale phase to the inhale phase of the subsequent cycle, where the pad has its minimal thickness. However, when the tactile stimulus gets weaker, the breath pacing effect is deteriorated.

A sleep aid device for inducing and/or manipulating sleep is disclosed in US 2007/0179334 A1. This device includes a fluid-filled mattress, a fluid pump sealably connected to the mattress, and a control module. The fluid pump modulates fluid into and/or out of the mattress, which may stimulate the feel and/or sound of a human breathing.

U.S. Pat. No. 5,395,301 teaches a kinesthetic system for promoting rhythmic breathing by tactile stimulation. U.S. Pat. No. 5,395,301 claims a method and a system for encouraging a desired breathing pattern, the system comprising a respiratory ventilator for respirating a patient according to the desired pattern, a kinesthetic device capable of being worn by the patient having a means for providing the patient with a non-driving cyclical tactile stroking sensation, the stroking sensation emulating human touch, and means for cyclically operating said kinesthetic device in synchronization with said respiratory ventilator so as to encourage the patient to breath in accordance with the desired breathing pattern.

International publication WO 86/02815 A1 discloses a mattress incorporating means to stimulate the heartbeat of an adult, the mattress comprises a sound chamber, means to stimulate the heartbeat and power means therefore. In addition means may be provided to stimulate the respiratory movements of an adult.

Document FR 2 834 875 discloses a rhythmic pillow to aid sleep and relaxation. The pillow is in two parts—a fixed section filled with foam or feathers, and an inflatable section connected by rubber tubes to a housing containing a small blower. The blower, which is electronically controlled, delivers air to the inflatable section of the pillow through two valves to produce either a gentle rising and falling motion or a side to side rocking motion.

Patent application GB 2 397 761 A pertains to a mattress for inducing a calming effect on a person using the mattress, which mattress comprises an upper portion for being laid upon by the person, and movement-creating means that causes the upper portion to rise and fall with a movement that is smooth and rhythmical and substantially the same as the rising and falling action of a mother's chest as the mother reclines and breathes with an infant resting on her chest.

United States patent application no. US 2010/0125226 A1 concerns a simple, portable, easy to operate device that helps the user to practice deep breathing techniques in their everyday life.

The German utility model DE 201 03 442 U1 relates to a pillow or a support for a pillow which is characterized in that its height changes periodically, comparable to a breathing movement.

German utility model DE 202 05 187 U1 discloses a mattress for infants, the mattress being characterized in that it includes means for continuously raising and lowering an area smaller than the contact area of an infant lying on the mattress, wherein the alternating up- and down movement is within a height of 1 to 5 cm within the breathing rhythm of a resting adult.

It is therefore an object of the present invention to provide a breath pacing apparatus providing a variable haptically perceivable feature according to a sequence of desired respiration cycles that enables the user to follow the respiration cycles easier than with known breath pacing apparatuses, even with increasing length of the respiration cycles.

It is another object of the present invention to create a corresponding method for pacing the respiration of a person, providing an output signal haptically perceivable during a sequence of desired respiration cycles that can be haptically perceived easily by a user even with increased length of the respiration cycles.

SUMMARY OF THE INVENTION

According to a first aspect of the present invention, this object is achieved by a breath pacing apparatus comprising a haptic output unit with a variable haptically perceivable feature, said haptic output unit being provided to change said haptically perceivable feature periodically according to a sequence of desired respiration cycles, wherein a characteristic of the change of said haptically perceivable feature is related to the length of the respiration cycles.

The invention is based on the concept that the perception of a variation of a haptically perceivable feature can be facilitated by influencing certain characteristics of this variation. This offers the possibility to follow the variation even in longer respiration cycles. For example, the amplitude of the variation of the feature within one cycle can be increased with each subsequent cycle so that the user can feel the difference between a maximum and minimum value more easily. However, other characteristics of the change of the haptically perceivable feature can be used within the scope of the present invention, like, for example, the magnitude of the change of the feature per time unit, that can be related to a smaller time scale compared to the length of the respiration cycle. Increasing the magnitude of change per time unit gives the user the feeling that the output signal changes "faster".

According to one preferred embodiment of the present invention, said haptically perceivable feature is changed within each respiration cycle between a minimum value and a maximum value, said characteristic of the change of said haptically perceivable feature being the difference between the maximum value and the minimum value.

According to another preferred embodiment of the invention, said characteristic is the magnitude of change of said haptically perceivable feature per time unit.

According to another preferred embodiment of the present invention, the magnitude of change of said haptically perceivable feature per time unit is varied in a non-linear fashion within a respiration cycle.

According to another preferred embodiment of the invention, the variable haptically perceivable characteristic is the size of the haptic output unit.

According to another preferred embodiment, the variable haptically perceivable characteristic is the thickness of the haptic output unit.

According to another preferred embodiment, the variable haptically perceivable characteristic is the shape, the weight, the hardness, and/or the surface texture of the haptic output unit.

For example, the shape of the haptic output unit may vary between different shapes, representing "maximum" and "minimum" values in the sense of the present invention. According to other examples, its weight may vary between a light and a heavy value, its hardness varies between a harder and a softer haptic impression, or its surface changes between a smooth surface and a rough surface. The haptic output unit is an inflatable wristband.

According to a second aspect of the present invention, a method for pacing the respiration of a person is provided, comprising:
  determining a sequence of desired respiration cycles, each cycle comprising an inhale phase and a subsequent exhale phase,
  generating an output signal haptically perceivable by a person during said sequence of desired respiration cycles, said output cycle changing periodically between a maximum value and a minimum value, each period corresponding to one respiration cycle,
  wherein a characteristic of the change of said output signal is related to the length of the respiration cycles.

According to a preferred embodiment of this method, the characteristic of the change of the output signal is the difference between the maximum value and the minimum value, as described above.

According to another preferred embodiment of this method, said characteristic of the change of the output signal is the magnitude of change per time unit.

Preferably the magnitude of change of the output signal per time unit is varied in a non-linear fashion within a respiration cycle.

This gives the opportunity to increase the change of the output signal at a transition point between two phases of the respiration cycle. For example, the maximum value of the output signal is reached at the transition between the inhale phase and the exhale phase. Increasing the change of the output signal at this transition point facilitates the perception of the transition, supporting the pacing effect.

According to a preferred embodiment of this method, the output signal is outputted by a haptic output unit.

According to another preferred embodiment, the output signal is represented by at least one of the following group:
  the size of said haptic output unit;
  the thickness of said haptic output unit;
  the shape of said haptic output unit;
  the weight of said haptic output unit;
  the hardness of said haptic output unit;
  the surface texture of said haptic output unit.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
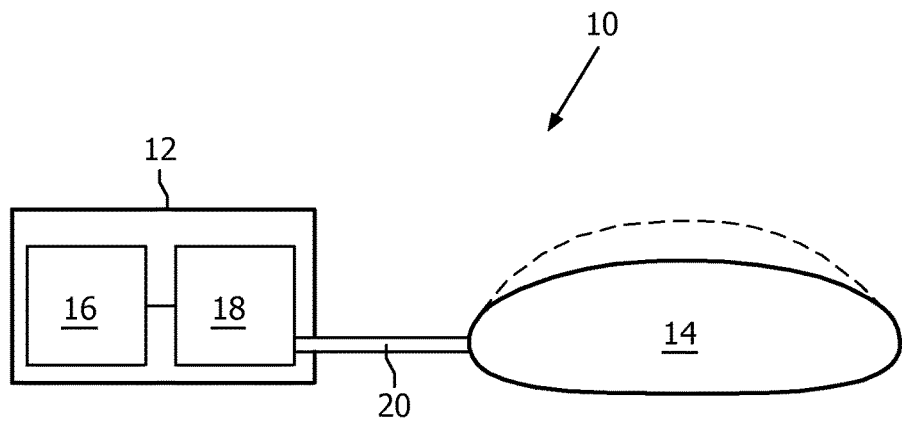
FIG. 1 is a schematic view of a breath pacing apparatus according to one embodiment of the present invention.

The breath pacing apparatus 10 in FIG. 1 is provided to pace the respiration of a person by determining a sequence of desired respiration cycles, each cycle comprising an inhale phase and a subsequent exhale phase. This sequence of desired respiration cycles is represented by an output signal that is haptically perceivable by the person, so that she/he can follow the respiration cycles easily. The output signal changes periodically between a maximum value and a minimum value, each period corresponding to one cycle, as will be further explained with reference to FIGS. 2 and 3. The person can feel the periodic change between the maximum and minimum values and adjust her/his own breath to the respiration rate generated by the breath pacing apparatus 10.

The breath pacing apparatus 10 comprises a controlling unit 12 and a haptic output unit 14 controlled by the controlling unit 12. The controlling unit 12 is disposed inside a casing and comprises a respiration cycle determining unit 16 and an actuating unit 18. The respiration cycle determining unit 16 determines a sequence of desired respiration cycles, each cycle comprising an inhale phase and a subsequent exhale phase. For this purpose the respiration cycle determining unit 16 may comprise a suitable electronic computing unit, storing means for storing a program for calculating the sequence, an electric output signal generation unit for generating an electric output signal corresponding to the predetermined or calculated respiration cycles, or the like.

The actuating unit 18 comprises means for generating a pneumatic pressure according to the electric signals received by the respiration cycle determining unit 16. That is, the actuating unit 18 converts the electric signals corresponding to the desired respiration cycles into pressure output signals. The pressure generated by the actuating unit 18 is applied to the haptic output unit 14 that is represented by a pad with a generally flat ellipsoid shape. This pad can be inflated by applying the pneumatic pressure generated by the actuating unit 18 so that the pad increases its size, especially its thickness in the vertical direction in FIG. 1. The inflated state is indicated by a dashed line in FIG. 1, while the deflated state is indicated by the continuous elliptical line showing the cross section of the haptic output unit 14. The air pressure is transferred from the actuating unit 18 to the haptic output unit 14 by a flexible hose 20 connecting the actuating unit 18 and the haptic output unit 14. The resulting thickness of the haptic output unit 14 is a feature representing an output signal that can be haptically perceived by a user. In use of the breath pacing apparatus 10 in a bedroom situation, the haptic output unit 14 will be disposed in bed so that it can be easily reached by a person lying therein and putting her/his hand on the pad to feel the change of its size according to the sequence of desired respiration cycles, while the controlling unit 12 will be disposed at another suitable place next to the bed. It is easily understood that the hose 20 should be long and flexible enough to place the haptic output unit 14 relatively independent from the controlling unit 12.

The operation of the breath pacing apparatus 10 in FIG. 1 will be explained in the following in view of FIG. 2.

Figure 2:
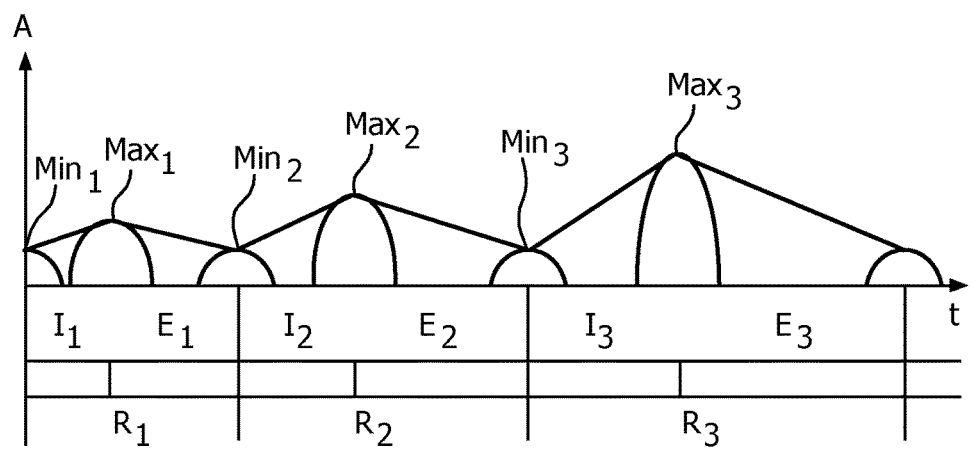
FIG. 2 is a diagram showing the operation of the breath pacing apparatus of FIG. 1.

The diagram in FIG. 2 represents a sequence of desired respiration cycles as generated by the controlling unit 12 in FIG. 1. The horizontal x-axis in FIG. 2 represents the time t, while the vertical y-axis represents the value A of the output signal, i.e. the thickness of the haptic output unit 14. The elevation of the top surface of the haptic output unit 14 is indicated schematically at some points of time to illustrate the "up" and "down" of the top surface of the pad representing the haptic output unit 14. This movement can be perceived by a user putting her/his hand on the pad.

The sequence of desired respiration cycles is indicated below the axis of time t. FIG. 2 shows three subsequent respiration cycles $R_1$, $R_2$, $R_3$. In this embodiment, each respiration cycle $R_1$, $R_2$, $R_3$ comprises an inhale phase $I_1$, $I_2$, $I_3$, followed by an exhale phase $E_1$, $E_2$, $E_3$. At the beginning of each respiration cycle $R_1$, $R_2$, $R_3$, the haptic output unit 14 has its minimal thickness, i.e. the output signal A has a minimal value. During the inhale phase $I_1$, $I_2$, $I_3$, the thickness increases up to a maximum value at the transition from the inhale phase $I_1$, $I_2$, $I_3$ to exhale phase $E_1$, $E_2$, $E_3$. During the following exhale phase $E_1$, $E_2$, $E_3$, the thickness decreases again to a minimal value of thickness. In the diagram the line connecting the maxima and minima of the output signal A in time t indicates the development of the output signal A that changes periodically between maximum and minimum values, each period corresponding to one respiration cycle $R_1$, $R_2$, $R_3$. For the sake of completeness it should be noted that the role of the phases $I_1$, $I_2$, $I_3$ and $E_1$, $E_2$, $E_3$ can be reversed within the scope of the present invention, in the sense that phases $I_1$, $I_2$, $I_3$ with increasing thickness are interpreted as exhale phases, while phases $E_1$, $E_2$, $E_3$ with decreasing thickness are interpreted as inhale phases.

To achieve a relaxing effect, the breathing sequence displayed by the desired respiration cycles $R_1$, $R_2$, $R_3$ should mimic the breathing sequence of a relaxed person as good as possible. For this reason it is advantageous that the respiration cycles $R_1$, $R_2$, $R_3$ do not have the same length but the length increases with each subsequent cycle, i.e. $R_1 < R_2 < R_3$ and so on, or to put it more generally: $R_n < R_{n+1}$, with n being a positive integer. With increasing length of the respiration cycles $R_1$, $R_2$, $R_3$, the length of the respective inhale phases $I_1$, $I_2$, $I_3$ and exhale phases $E_1$, $E_2$, $E_3$ also increases.

With increasing length of the respiration cycles $R_1$, $R_2$, $R_3$ and constant difference of the minimum and maximum values of the output signal A over the whole sequence, i.e. within all respiration cycles $R_1$, $R_2$, $R_3$ and following, the problem arises that it becomes more difficult for a person to feel the periodic change of the output signal A. This is mainly due to the fact that the output signal variation per time unit becomes smaller and the user has the feeling that the amplitude changes very "slow". It is particularly relevant not to miss the transitions between the inhale phases $I_1$, $I_2$, $I_3$ and the exhale phases $E_1$, $E_2$, $E_3$ to adapt the own respiration rate to the respiration cycles determined by the breath pacing apparatus 10, and consequently it is elementary for the pacing result to feel when the output signal a reaches its maximum values and minimum values.

For this reason the present invention proposes to relate one characteristic of the change of the output signal A to the length of the respiration cycles $R_1$, $R_2$, $R_3$. In the present embodiment shown in FIG. 2, this characteristic is represented by the difference between the maximum values and the minimum values of the output signal A. For example, in FIG. 2, the maximum values $Max_1$, $Max_2$, $Max_3$ within each respiration cycle $R_1$, $R_2$, $R_3$ of the output signal A increase with each respiration cycle $R_1$, $R_2$, $R_3$, so that $Max_1 < Max_2 < Max_3$. In the present example the minimum values $Min_1$, $Min_2$, $Min_3$ stay the same for each respiration cycle $R_1$, $R_2$, $R_3$, i.e. $Min_1 = Min_2 = Min_3$, so that the differences between the maximum values and the minimum values increase, and $Max_1 - Min_1 < Max_2 - Min_2$, and so on. This increase of the difference between the maximum values $Max_1$, $Max_2$, $Max_3$ and the minimum values $Min_1$, $Min_2$, $Min_3$ can be haptically perceived easily by a person. One further effect is that the haptic output unit 14 mimics the natural respiration rate of a relaxing human more naturally and the differences between the maximum values and the minimum values of the output signal A are increased so that the respiration becomes "deeper".

It is noted that the difference between the maximum value Max and the minimum value $Min_n$ of the output signal A, that represents the thickness as one haptically perceivable feature of the haptic output unit 14, is only one possible characteristic of the change of this haptically perceivable feature that can be linked to the length of the respiration cycles $R_1$, $R_2$, $R_3$. However, there are other possibilities and examples of characteristics of the change of this feature. In FIG. 2, one can see that the steepness of the ascending slope from $Min_n$ to Max in each respiration cycle $R_n$, n=1 to 3, only slightly increases, as well as the descending slope from $Max_n$ to $Min_{n+1}$ during the exhale phase $E_n$, although the length of the respiration cycles increases. However, it is possible to further increase the steepness of the ascending slope and the descending slope so that the magnitude of change of the haptically perceivable feature (or the output signal) per time unit can be easier perceived by a person, getting the impression that the thickness of the haptic output unit changes "faster". In this embodiment the change between the maximum values and minimum values may still be linear, as in FIG. 2.

Figure 3:
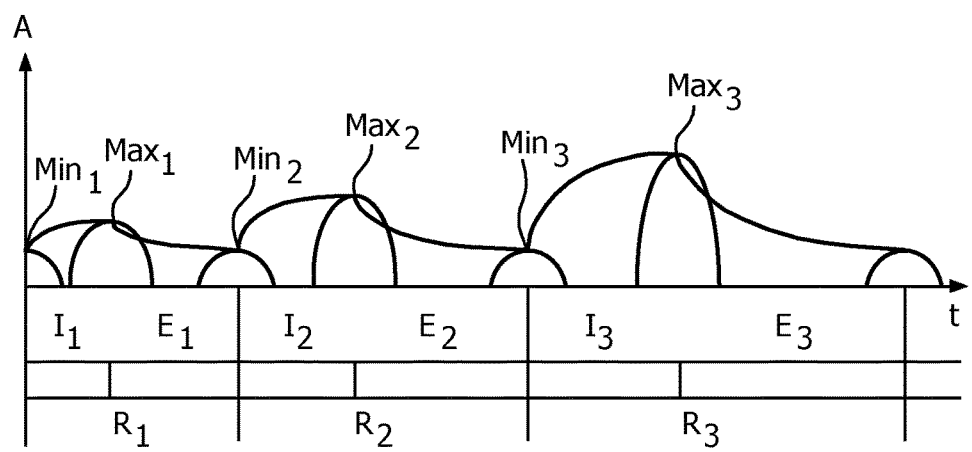
FIG. 3 is another diagram to show another operation mode of a breath pacing apparatus according to FIG. 1.

FIG. 3 shows another possibility to change the haptically perceivable feature (or output signal) of the haptic output unit 14. The operation mode shown in FIG. 3 can be another operation mode of the breath pacing apparatus 10 in FIG. 1, or can be processed by another breath pacing apparatus. In this embodiment the magnitude of change of the output signal is varied within each respiration cycle $R_1$, $R_2$, $R_3$ so that there is a non-linear change between the minimum value and the maximum value, respectively. At the begin beginning of each cycle $R_1$, $R_2$, $R_3$, the thickness of the haptic output unit 14 is increased with a stronger rate to higher values, and after that instant increase of thickness, it increases slower to reach the maximum value at the end of the inhale phase $I_1$, $I_2$, $I_3$. After reaching the maximum, the thickness instantly becomes smaller, then developing slower towards the minimum value of the next respiration cycle again. In other words, the magnitude of change of the thickness as the haptically perceivable feature (or output signal) of the haptic output unit 14 increases immediately after reaching a minimum value or a maximum value, respectively. This behavior of the haptic output unit 14 can be perceived easier than a "smooth" and linear development of the thickness, especially at the transition points between the inhale phases $I_1$, $I_2$, $I_3$ and the exhale phases $E_1$, $E_2$, $E_3$ that determine the respiration rhythm.

In the example of FIG. 3, the difference between the maximum value and the minimum value of the thickness also increases with each respiration cycle $R_1$, $R_2$, $R_3$. However, it is possible to keep this difference constant and only to increase the magnitude of change per time unit within each respiration cycle $R_1$, $R_2$, $R_3$. This should be considered especially in view of the fact that the volume of an inflatable pad, like in the embodiment of FIG. 1, is limited, and the increase in the variation of thickness of the pad is limited to some extent.

There are other possibilities to change the variation of thickness within the respiration cycles $R_1$, $R_2$, $R_3$. For example, the "smoothness" of the variation can be further influenced by introducing small changes of the thickness variation around a generally smooth curve, like they are represented in FIGS. 2 and 3. These variations could be felt as small vibrations of the pad. The intensity of these vibrations can also be varied to indicate a transition between different phases within the respiration cycle $R_1$, $R_2$, $R_3$.

It is understood that other haptically perceivable features of the haptic output unit 14 can be used as output signals than the thickness of the pad used in this embodiment. For example, the general size, i.e. the outer diameter represents another perceivable feature. It could also be considered to change the shape of the haptic output unit between different shapes that represent "maximum" values and "minimum" values of the output signal. For example, the haptic output unit 14 could comprise a certain curvature that increases and decreases periodically between a maximum curvature and a minimum curvature, or the like. Other examples of haptically perceivable features of the haptic output unit 14 that can be used in this context are its weight (varying between "light" and "heavy"), its hardness (varying between "hard" and "soft") and its surface texture (varying between "smooth" and "rough").

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A breath pacing apparatus, comprising:
   a haptic output unit with a variable haptically perceivable feature,
   said haptic output unit being configured to change said haptically perceivable feature according to a sequence of respiration cycles, each respiration cycle in said sequence having a duration a respective maximum value and a respective minimum value,
   wherein a characteristic of the change of said haptically perceivable feature is a function of a difference in duration between duration of a current respiration cycle in the sequence and duration of at least one other respiration cycle in the sequence that immediately precedes or follows the current respiration cycle; and
   a respiration cycle determiner configured to generate the sequence of respiration cycles,
   wherein the respective maximum values of the respiration cycles in the sequence increase with each subsequent respiration cycle, and wherein respective differences between the respective maximum values and the respective minimum values increase with each subsequent respiration cycle.

2. The breath pacing apparatus according to claim 1, wherein said haptically perceivable feature is changed within each respiration cycle in said sequence between a minimum value of each respiration cycle and a maximum value of each respiration cycle,
   said characteristic of the change of said haptically perceivable feature being a range between a size of the maximum value and a size of the minimum value for a respiration cycle in the sequence.

3. The breath pacing apparatus according to claim 1, wherein said characteristic of the change of said haptically perceivable feature is a function of a magnitude of change of said haptically perceivable feature per time unit.

4. The breath pacing apparatus according to claim 3, wherein the magnitude of change of said haptically perceivable feature per time unit is varied in a non-linear fashion within a respiration cycle of the sequence.

5. The breath pacing apparatus according to claim 1, wherein the variable haptically perceivable feature is a size of the haptic output unit.

6. The breath pacing apparatus according to claim 1, wherein the variable haptically perceivable feature is a thickness of the haptic output unit.

7. The breath pacing apparatus according to claim 1, wherein the variable haptically perceivable feature includes at least one of a weight, a hardness, and a surface texture of said haptic output unit.

8. A method for pacing a respiration of a person, comprising acts of:
   determining a sequence of respiration cycles, each respiration cycle in said sequence having a duration, a respective maximum value and a respective minimum value; and
   generating an output signal haptically perceivable by the person during said sequence of respiration cycles, said output signal being provided by a haptic output unit, and said output signal configured to change periodically between the respective maximum value and the respective minimum value, each period of change corresponding to one respiration cycle, wherein a characteristic of the change of said output signal is a function of a difference in duration between duration of a current respiration cycle in the sequence and duration of at least one other respiration cycle in the sequence that immediately precedes or follows the current respiration cycle, and wherein the respective maximum values of the respiration cycles in the sequence increase with each subsequent respiration cycle, and wherein respective differences between the respective maximum values and the respective minimum values increase with each subsequent respiration cycle.

9. The method according to claim 8,
wherein said characteristic of the change of said output signal is a range between a size of the maximum value and a size of the minimum value for the current respiration cycle.

10. The method according to claim 8,
wherein said characteristic of the change of said output signal is a magnitude of change per time unit.

11. The method according to claim 10,
wherein the magnitude of change of said output signal per time unit is varied in a non-linear fashion within a respiration cycle of the sequence.

12. The method according to claim 8, wherein said output signal comprises at least one of:
a weight of said haptic output unit;
a hardness of said haptic output unit; and
a surface texture of said haptic output unit.

13. A computer-readable storage-medium that is not a transitory propagating signal or wave, the medium comprising control information for controlling a breath pacing apparatus for performing the method of claim 8.

14. A method for pacing a respiration of a person, comprising acts of:
determining a sequence of respiration cycles, each respiration cycle in said sequence having a duration, a respective maximum value and a respective minimum value; and
generating an output signal haptically perceivable by the person during said sequence of respiration cycles, said output signal being provided by a haptic output unit, and said output signal configured to change between the respective maximum value and the respective minimum value for each of the respiration cycles in the sequence,
wherein a characteristic of the change of said output signal for each of the respiration cycles in the sequence is a function of a difference in duration between duration of a current respiration cycle in the sequence and duration of at least one other respiration cycle in the sequence that immediately precedes or follows the current respiration cycle, and
wherein the respective maximum values of the respiration cycles in the sequence increase with each subsequent respiration cycle, and wherein respective differences between the respective maximum values and the respective minimum values increase with each subsequent respiration cycle.

15. The method according to claim 14,
wherein said characteristic of the change of said output signal is a magnitude of change per time unit.

16. The method according to claim 15,
wherein the magnitude of change of said output signal per time unit is varied in a non-linear fashion within a respiration cycle of the sequence.

17. The method according to claim 14, wherein said output signal comprises at least one of:
a weight of said haptic output unit;
a hardness of said haptic output unit; and
a surface texture of said haptic output unit.

18. A breath pacing apparatus, comprising:
a haptic output unit including a variable haptically perceivable feature, said haptic output unit configured to change said haptically perceivable feature according to a sequence of respiration cycles, wherein each respiration cycle in said sequence has a duration, wherein each respiration cycle in said sequence has a respective maximum value and a respective minimum value,
wherein a characteristic of the change of said haptically perceivable feature is related to a function of a difference in duration between duration of the current respiration cycle in the sequence and duration of at least one other respiration cycle in the sequence that immediately precedes or follows the current respiration cycle; and
a respiration cycle determiner configured to generate the sequence of respiration cycles,
wherein the respective maximum values of the respiration cycles in the sequence increase with each subsequent respiration cycle, and wherein respective differences between the respective maximum values and the respective minimum values increase with each subsequent respiration cycle.

19. The breath pacing apparatus of claim 18, wherein the respective minimum values of the respiration cycles in the sequence are the same.

* * * * *